United States Patent [19]

Jarrott et al.

[11] 4,094,964

[45] June 13, 1978

[54] CLONIDINE ASSAY

[75] Inventors: Bevyn Jarrott, Nutley; Sidney Spector, Livingston, both of N.J.

[73] Assignee: Hoffmann-La Roche Inc., Nutley, N.J.

[21] Appl. No.: 795,576

[22] Filed: May 10, 1977

[51] Int. Cl.$^2$ .................... G01N 33/16; A61K 43/00; C07G 7/00; A61K 39/00

[52] U.S. Cl. .................................... 424/1; 23/230 B; 260/112 R; 424/12; 424/251; 544/264

[58] Field of Search .......................... 424/1, 12, 251; 23/230 B; 260/254, 256.4, 112 R

[56] References Cited

PUBLICATIONS

Frydman, Chemical Abstracts, vol. 84, No. 9, Mar. 1, 1976, p. 5, Abstract No. 53715c.

Rouot et al., Chemical Abstracts, vol. 85, No. 9, Aug. 30, 1976, p. 17, Abstract No. 56532x.

*Primary Examiner*—Benjamin R. Padgett
*Assistant Examiner*—Christine M. Nucker
*Attorney, Agent, or Firm*—Samuel L. Welt; George M. Gould; Raymond R. Wittekind

[57] ABSTRACT

A sensitive immunoassay for clonidine, 2-(2,6-dichloroanilino)-2-imidazoline hydrochloride is described. To prepare the clonidine selective antiserum, an antigen is made comprising 4-[[6-[2,4-dichloro-3(4,5-dihydro-1H-imidazol-2-yl)amino]hydroxyphenyl]azo]-benzoic acid covalently bonded to an immunogenic carrier material through a peptide bond formed from said carboxyl group and amino groups contained in said immunogenic carrier material and the antigen is injected into a suitable host animal to elicit the desired antiserum.

8 Claims, No Drawings

CLONIDINE ASSAY

BACKGROUND OF THE INVENTION

Clonidine is a unique centrally-acting antihypertensive used extensively in clinical medicine. See "Catapres In Hypertension," M. E. Conolly, Ed., Butterworth and Co., London, England, 1970. Due to the high potency exhibited by the drug coupled with individual blood pressure responses shown by patients, it is desirable to monitor the level of clonidine in the biological fluids of patients so that the proper dose regimen may be determined. Thus a sensitive method for the determination of clonidine in body fluids would represent a significant advance in the art.

DESCRIPTION OF THE INVENTION

The present invention relates in one aspect to a novel antigen useful in eliciting antiserum selective to clonidine. The antigen comprises 4-[[6-[2,4-dichloro-3-(4,5-dihydro-1H-imidazol-2-yl)amino]hydroxyphenyl]azo]-benzoic acid covalently bonded to an immunogenic carrier material through a peptide bond formed from the carboxyl group of the hapten and amino groups contained in said immunogenic carrier material.

As used herein the term "immunogenic carrier material" is meant to include those materials which have the property of independently eliciting an immunogenic response in a host animal when injected therein and which can be coupled by covalent bonding to said hapten. Suitable carrier materials include, for example, materials such as proteins, natural or synthetic polymeric compounds such as polypeptides, e.g., polylysine and the like. A particularly preferred carrier material for the practice of the present invention is protein.

The identity of the protein carrier material utilized in the preparation of the instant antigen is not narrowly critical. Example of preferred proteins useful in the practice of this invention include serum proteins, preferably mammalian serum proteins, such as, for example, human gamma globulin, human serum albumin, rabbit serum ablumin, bovine gamma globulin and bovine serum albumin. Other suitable protein products will be suggested to one skilled in the art. It is generally preferred that proteins be utilized which are foreign to the animal host in which the resulting antigen will be employed.

A further aspect of the present invention relates to the novel hapten 4-[[6-[2,4-dichloro-3-(4,5-dihydro-1H-imidazol-2-yl)amino]hydroxyphenyl]azo]benzoic acid of the formula

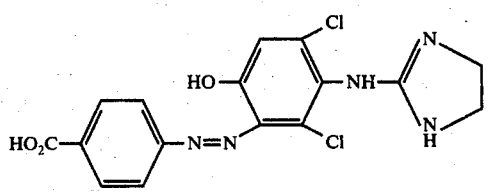

and salts therefor.

The azo compound is conveniently prepared by coupling 4-carboxybenzenediazonium halide, prepared by diazotization of 4-aminobenozic acid, with the known metabolite, 2-(2,6-dichloro-4-hydroxyanilino)-2-imidazoline, of clonidine (D. Rehbinder and W. Deckers, Arzneimittelforsch, 19, 169 (1969)) by methods well-known in the art. See, for example, L. F. Fieser and M. Fieser, "Organic Chemistry", Reinhold Publishing Corporation, New York, N.Y., Pages 605 and 618 to 622.

In the preferred embodiment, 4-aminobenozic acid is treated with about 4% aqueous sodium nitrite in the presence of about 1 M hydrochloric or hydrobromic acid at a reduced temperature of about 0° C. followed by about 2% aqueous ammonium sulfamate, also at about 0° C., to decompose excess nitrous acid to afford 4-carboxybenzenediazonium chloride or bromide. The pH of the solution is then adjusted to about 10 by means of about 5 M sodium or potassium hdyroxide solution, and 2-(2,6-dichloro-4-hydroxyanilino)-2-imidazoline hydrobromide or hydrochloride is treated with the resulting alkaline diazotization mixture to give the hapten, 4-[-6-[2,4-dichloro-3-(4,5-dihydro-1H-imidazol-2-yl)amino]hydroxyphenyl]azo]benzoic acid.

The hapten so obtained can then be coupled to the immunogenic carrier material by any of the procedures known in the art for this purpose. One preferred method is to directly couple the hapten to the immunogenic carrier material using a water soluble carbodiimide coupling reagent. A preferred carbodiimide coupling reagent is 1-ethyl-3-(3-dimethylaminopropyl)carbodiimide. The coupling reaction to prepare the antigen is carried out in aqueous medium at a pH in the range of about 4 to 8, preferably at a pH of about 5.5.

The antigen of the present invention may then be utilized to induce formation of clonidine specific antibodies in the serum of host animals by injecting the antigen in such host repeatedly over a period of time. The collected serum may be used per se as a clonidine specific antiserum or, if desired, the antibodies therein may be further purified by precipitation with a neutral salt solution followed by dialysis and column chromatography.

Suitable host animals for preparing antiserum to clonidine include mammals such as rabbits, horses, goats, guinea pigs, rats, cows, sheep and the like. The resulting antibodies will have a multiplicity of active sites which will selectively complex with clonidine and the antigen of the present invention.

The formation of clonidine specific antibodies in the host animals may be monitored by taking blood samples from the host animal and adding it to an amount of the labelled hapten. The presence of a labelled hapten-antibody complex indicates antibody activity. The antigen treatment of the animal can be continued until the antibody titre reaches a desired level of activity. For the purpose of this application the antibody titre is defined as being the maximum dilution of the antibody to precipitate 50% of the added labelled hapten.

The specific antibodies of the present invention are useful as reagents in biochemical assays for the determination of the presence of clonidine in biological fluids such as plasma and urine, and tissue extracts. A particularly preferred assay procedure is the radioimmunoassay procedure such as described in U.S. Pat. No. 3,709,868. Preferred labelled clonidine for use in immunoassay include isotopically labelled clonidine, particularly clonidine $^3H$ or $^{14}C$ as well as clonidine labelled with an electron spin resonance group. Examples of the use of various electron spin resonance labelled molecules in bioassays are to be found in U.S. Pat. Nos. 3,453,288; 3,481,952 and 3,507,876.

The radioimmunoassay method is preferred for the determination of clonidine. It is a sensitive, simple and rapid procedure. Thus it is possible to determine as little as 500 pg of clonidine in tissue or body fluid using 50 mg of tissue or 0.1 ml of plasma with clonidine $^{14}$C as the tracer.

EXAMPLE 1

Preparation of 4-[[6-[2,4-dichloro-3-(4,5-dihydro-1H-imidazol-2-yl)amino]hydroxyphenyl]azo]benzoic acid.

A 4% aqueous solution of sodium nitrite (3 ml) was cooled in an ice-bath and then added to a solution of 4-aminobenzoic acid (30 mg) in 1 M hydrochloric acid (3 ml), also cooled in an ice-bath. The solution was allowed to stand for 1 minute at 0° C. and then 2% aqueous ammonium sulfamate (3 ml) was added to decompose excess nitrous acid. Upon cessation of the effervescence (ca 1 min.), 5 M sodium hydroxide solution was added dropwise with stirring to the solution maintained at 0° C. until the pH reached a value of about 10. The resulting yellow amber solution was allowed to stand at 0° C. for 1 hr. The cold diazotization mixture was added dropwise, with stirring, to a solution of 2-(2,6-dichloro-4-hydroxyanilino)-2-imidazoline hydrobromide (20 mg) in water (5 ml). The reaction mixture was stirred at room temperature for 2 hours to afford the azo compound.

EXAMPLE 2

Attachment of 4-[[6-[2,4-dichloro-3-(4,5-dihydro-1H-imidazol-2-yl)amino]hydroxyphenyl]azo]benzoic acid to bovine serum albumin.

The solution of 4-[[6-[2,4-dichloro-3-(4,5-dihydro-1H-imidazol-2-yl)amino]hydroxyphenyl]azo]benzoic acid obtained above was added dropwise, with stirring, to a solution of 1-ethyl-3-(3-dimethylaminopropyl)carbodiimide (10 mg), bovine serum albumin (10 mg) and distilled water (5 ml) at room temperature. The reaction mixture was stirred overnight at room temperature protected from light. The solution was transferred into Spectropor No. 2 dialysis tubing, diazlyzed against phosphate buffer solution (pH 7.4) for 48 hours and freeze dried to give about 30 mg of bovine serum albumin conjugate.

The protein content of the conjugate was determined by the method of O. H. Lowry, et al., J. Biol. Chem., 193, 265 (1951), by untraviolet spectroscopy and by measurement of the residual free amino groups in the conjugate by the method of A.F.S.A. Habeeb, Anal. Biochem., 14, 328 (1965).

EXAMPLE 3

Immunization with 4-[[6-[2,4-dichloro-3-(4,5-dihydro-1H-imidazol-2-yl)amino]hydroxyphenyl]azo]benzoic acid bovine serum albumin conjugate.

New Zealand albino rabbits were immunized with 4-[[6-[2,4-dichloro-3-(4,5-dihdyro-1H-imidazol-2-yl)amino]hydroxyphenyl]azo]benzoic acid bovine serum albumin conjugate from Example 2 once every 4 weeks. The immunogen (1 mg) was dissolved in phosphate-buffered saline (pH 7.4) (1 ml) and emulsified with complete Freund's adjuvant (1 ml). The emulsion (1 ml) was injected into the four foot pads (0.25 ml/pad). Bleedings were taken from the central ear artery 1 week after the last booster immunization. The blood was allowed to clot overnight at 4° C. and then centrifuged at 2,000 rpm for 15 minutes to separate serum.

EXAMPLE 4

Radioimmunoassay with antisera to 4-[[6-[2,4-dichloro-3-(4,5-dihydro-2-yl)amino]hydroxyphenyl]azo]benzoic acid bovine serum albumin conjugate.

The antiserum of Example 3 as used for the radioimmunoassay was diluted with normal rabbit serum which was diluted with phosphate-buffered saline, pH 7.4, at 1:10-dilution. To determine the antibody titre of antiserum, 0.1 ml of various dilutions of the antiserum was incubated in an assay tube (10 × 75 mm) with 2 ng of clonidine $^{14}$C approximately 3,000 cpm at 4° C. for about 18 hours. The volume was adjusted to 0.5 ml with phosphate-buffered saline, pH 7.4, which is the optimal pH for the assay. The antibody bound clonidine was separated from free clonidine by the addition of saturated ammonium sulfate which was adjusted to pH 7.4 with ammonium hydroxide as described by Farr, J. Infect. Dis 103, 239 (1958). After 2 washings with 50% saturated ammonium sulfate, the precipitate was dissolved in 0.5 ml of water. The content of the tube was transferred to counting vial and the tube was then washed 4 times with 3 ml of Riafluor. The 12 ml washings were all collected in the vial. The radioactivity was then counted with a Beckman liquid scintillation counter. The dilution of the antiserum chosen for further studies was 1:50.

Appropriate volume of phosphate-buffered saline, pH 7.4 was added to all tubes containing 0.1 ml of the antiserum to make a final incubation volume of 0.5 ml. To the tubes were added 100 ul of clonidine-$^{14}$C and various quantities ranging from 100 ng to 500 pg of clonidine, 2-(2,6-dichloro-4-hydroxyanilino)-2-imidazoline (4-hydroxyclonidine), 2-(2,6-dichloro-4-sulfonamidoanilino)-2-imidazoline (4-sulfonamidoclonidine),2-(2-chloro-3-methylanilino)-2-imidazoline, 2-(2-chloro-4-methylanilino)-2-imidazoline, 2-(2-chloro-6-methylanilino)-2-imidazoline, 2-anilino-2-imidazoline, 2-(2,6-dichloro-anilino)-2-methyl-2-imidazoline (2-methylclonidine), 2-(2,6-dichloroanilino)-1-methyl-2-imidazoline (1-methylclonidine), 1-acetamido-2-(2,6-dichloroanilino)-2-imidazoline (1-acetamidoclonidine), 2-(2,6-dichloroanilino)-2-pyrroline, 2-(2,6-dichloroanilino)-2-oxazoline, 2-(2,6-dichloroanilino)-2-benzimidazole, 2-(2,6-dichloroanilino)-1,3-dimethylquanidine, 2-(2,6-dichloroanilino)-1-methylguanidine, 2-(2,6-dichloroanilino)quanidine, aniline or 2-(2,6-dichlorobenzyl)-2-imidazoline. The tubes were then incubated for about 18 hours at 4° C. followed by precipitation with ammonium sulfate.

A standard curve for plasma was obtained by adding known amounts of clonidine in 10 ul of normal rabbit plasma to the assay tubes by adjusting the volume to 0.5 ml with phosphate-buffered saline, pH 7.4.

A computer program was utilized to obtain the standard curves.

RESULTS

Sensitivity of the radioimmunoassay.

The antibody of the sera of rabbits immunized with the clonidine bovine serum albumin immunogen was determined by the bonding of clonidine-$^{14}$C. Ouchterlony gel plates also indicated the presence of the antibody in sera of rabbits immunized with the conjugated clonidine. As little as 500 pg of clonidine can be detected by the antiserum of a rabbit immunized with 4-[[-6-[2,4-dichloro-3-(4,5-dihydro-1H-imidazol-2-yl)amino]hydroxyphenyl]azo]benzoic acid bovine serum albumin immunogen. The assay is linear up to 100 ng.

Specificity of the radioimmunoassay.

The specificity of the antibody in the antiserum of rabbit immunized by the clonidine bovine serum albumin immunogen was determined by incubating the antiserum with 2-(2,6-dichloro-4-hydroxyanilino)-2-imidazoline (4-hydroxyclonidine), 2-(2,6-dichloro-4-sulfonamidoanilino)-2-imidazoline (4-sulfonamidoclonidine), 2-(2-chloro-3-methylanilino)-2-imidazoline, 2-(2-chloro-4-methylanilino)-2-imidazoline, 2-(2-chloro-6-methylanilino)-2-imidazoline, 2-anilino-2-imidazoline, 2-(2,6-dichloroanilino)-2-methyl-2-imidazoline (2-methylclonidine), 2-(2,6-dichloroanilino)-1-methyl-2-imidazoline (1-methylclonidine), 1-acetamido-2-(2,6-dichloroanilino)-2-imidazoline (1-acetamidoclonidine), 2-(2,6-dichloroanilino)-2-pyrroline, 2-(2,6-dichloroanilino)-2-oxazoline, 2-(2,6-dichloroanilino)-2-benzimidazole, 2-(2,6-dichloroanilino)-1,3-dimethylguanidine, 2-(2,6-dichloroanilino)-1-methylguanidine, 2-(2,6-dichloroanilino)guanidine, aniline or 2-(2,6-dichlorobenzyl)-2-imidazoline in the presence of labelled clonidine. Clonidine produced a 50% inhibition of binding of clonidine-$^{14}$C to the antibody at a concentration of 25 nM. The antibody failed to recognize 2-anilino-2-imidazoline, 2-(2,6-dichloroanilino)-2-methyl-2-imidazoline, 2-(2,6-dichloroanilino)-1-methyl-2-imidazoline, 2-(2,6-dichloro-anilino)-2-oxazoline, 2-(2,6-dichloroanilino)-1,3-dimethylguanidine, 2-(2,6-dichloro-anilino)guanidine, aniline and 2-(2,6-dichlorobenzyl)-2-imidazoline. In order to obtain clonidine-$^{14}$C antibody complex formation, concentrations of 2-(2,6-dichloroanilino)-2-pyrroline and 2-(2,6-dichloroanilino)-1-methylguanidine of about 40 times that of clonidine are required. The antibody recognized 2-(2,6-dichloro-4-hydroxyanilino)-2-imidazoline, 2-(2,6-dichloro-4-sulfonamidoanilino)-2-imidazoline, 2-(2-chloro-3-methylanilino)-2-imidazoline, 2-(2-chloro-4-methylanilino)-2-imidazoline, 2-(2-chloro-6-methylanilino)-2-imidazoline and 1-acetamido-2-(2,6-dichloro)-2-imidazoline.

We claim:

1. An antigen consisting essentially of a hapten, 4-[[6-[2,4-dichloro-3-(4,5-dihydro-1H-imidazol-2-yl)amino]-hydroxyphenyl]azo]benzoic acid and acid addition salts thereof, covalently bonded to an immunogenic carrier material through peptide bonds formed between said carboxyl group and amino groups on said immunogenic carrier material.

2. The antigen of claim 1 wherein said immunogenic carrier material is bovine serum albumin.

3. The antigen of claim 1 wherein said hapten is 4-[[6-[2,4-dichloro-3(4,5-dihydro-1H-imidazol-2-yl)amino]-hydroxyphenyl]azo]benzoic acid.

4. An antibody specific to clonidine prepared by innoculating a host animal with an antigen consisting essentially of a hapten, 4-[[6-[2,4-dichloro-3-(4,5-dihydro-1H-imidazol-2-yl)amino]hydroxyphenyl]azo]-benzoic acid and acid addition salts thereof, covalently bonded to an immunogenic carrier material through peptide bonds formed between said carboxyl group and amino groups on said immunogenic carrier material and collecting the serum from said host animal.

5. The antibody of claim 4 wherein said antigen consists essentially of 4-[[6-[2,4-dichloro-3-(4,5-dihydro-1H-imidazol-2-yl)amino]hydroxyphenyl]azo]benzoic acid covalently bonded to bovine serum albumin.

6. A method for the assay of clonidine in a sample, which method comprises mixing said sample with a known amount of labelled clonidine and an antibody which will selectively complex with clonidine, measuring the degree of binding of said labelled clonidine compound with said antibody, and determining the amount of clonidine present in said sample by comparing said degree of binding to a standard curve obtained by mixing known amount of clonidine with fixed amounts of said labelled clonidine and said antibody and determining the degree of binding for each known amount of clonidine.

7. The method of claim 6 wherein said labelled clonidine is clonidine $^{14}$C.

8. A hapten of the formula

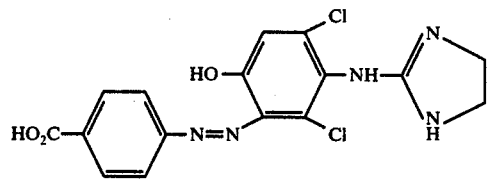

and salts thereof.

* * * * *